United States Patent
Kraus et al.

(10) Patent No.: US 8,340,249 B2
(45) Date of Patent: *Dec. 25, 2012

(54) REAL-TIME DOSIMETRY SYSTEM, RTDS

(75) Inventors: Thomas Kraus, Nashville, TN (US); Steve Szeglin, Nashville, TN (US)

(73) Assignee: Best Medical International, Springfield, VA (US)

( * ) Notice: Subject to any disclaimer, the term of this patent is extended or adjusted under 35 U.S.C. 154(b) by 119 days.

This patent is subject to a terminal disclaimer.

(21) Appl. No.: 12/795,967

(22) Filed: Jun. 8, 2010

(65) Prior Publication Data

US 2012/0177184 A1 Jul. 12, 2012

(51) Int. Cl.
*H05G 1/42* (2006.01)

(52) U.S. Cl. .......................................... 378/97; 378/64
(58) Field of Classification Search .................. 378/64, 378/97
See application file for complete search history.

(56) References Cited

U.S. PATENT DOCUMENTS 6,614,876 B1 * 9/2003 Kirk ................................ 378/64

* cited by examiner

*Primary Examiner* — Courtney Thomas
(74) *Attorney, Agent, or Firm* — Team Best Legal Dept.; Oneal R. Mistry

(57) ABSTRACT

Real-Time Dosimetry System, RTDS, is dose measurement system consisting of an ionization chamber and electrometer with the ability to measure, record, and display the high radiation doses required to meet approved standards for sterilization of medical, industrial and food products.

10 Claims, 5 Drawing Sheets

FIG.4
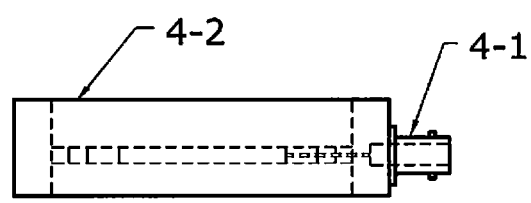
FIG.4A
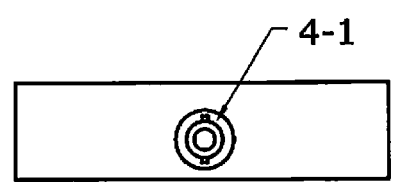
FIG.4C
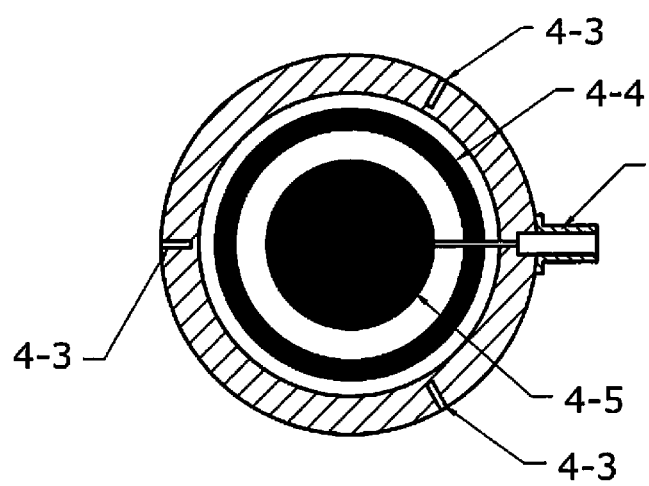
FIG.4B
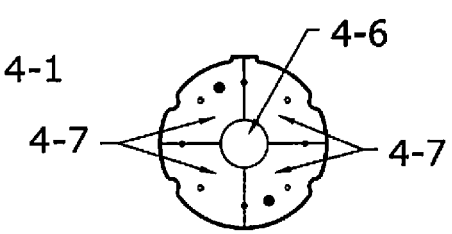
FIG.4D

REAL-TIME DOSIMETRY SYSTEM, RTDS

CROSS REFERENCE TO RELATED APPLICATION

[NONE]

FIELD OF THE INVENTION

This invention is related to irradiation of blood by using x-ray irradiation of blood plasma sanctioned by the U.S. Food and Drug Administration.

BACKGROUND

X-ray irradiation is used to help eliminate the chance of transfusion-induced diseases. The dose and resulting dose distribution must meet U.S. Food and Drug Administration criterion. The X-ray radiation must be precisely controlled and applied in order to meet and comply with existing regulatory requirements. X-ray radiation has several benefits over the gamma ray irradiation, electron beam application and other types of blood sanitization. X-ray irradiation equipment is relatively safe to handle in all types of environments as compared to other types of irradiators. X-ray irradiation equipment is easy to use and easily controlled in various application. However, existing X-ray irradiation equipment does not accurately measure the dose given during blood plasma irradiation nor does it monitor X-ray beam characteristics that would assure uniform irradiation of the blood plasma. X-ray doses are measured only by a given time of exposure, and not by accurately measuring or monitoring the X-ray beam.

There are times when blood plasma is not properly irradiated and not properly cleansed. Accordingly, there is a need to measure the high doses required during blood irradiation and to provide verification that the blood has received a certain minimum amount of dose (exposure) and has not exceeded a certain maximum amount of dose. Furthermore, there is a need for a system can be used to monitor irradiation output and automatically increase or decrease irradiation time as required to deliver a precise radiation dose, and to monitor irradiation beam characteristics like flatness and symmetry.

SUMMARY OF THE INVENTION

According to one general aspect, an apparatus to accurately measure blood irradiation comprising an ion chamber used to measure x-rays being radiated from a x-ray source, an electrometer connected to said ion chamber used to calculate the amount of dose applied to an object, a storage medium used to store information including a blood bag identification, a bag volume, a dose amount, date, and time; and said storage medium calculates minimum dose time to provide an energy efficient irradiation system, wherein said storage medium takes said bag volume and calculate the minimum dose time. Wherein said ion chamber may intercept and entire or partial amount of x-ray radiation beam to determine actual dose received. The apparatus further comprising said ion chamber may connect to a plurality of ion chambers in series or parallel and measure dose while irradiation is present. The apparatus further comprising said storage medium used to display the amount of dose received to said object on a display apparatus and allowing a user to control a graphical user interface system to increase or decrease the dose. The apparatus further comprising said ion chamber can be designed to conform to any shape in a radiation chamber to allow proper passage of radiation.

In another general aspect there is provided a method to accurately measure blood irradiation, the method comprising measuring the x-ray being radiated from a x-ray source, calculating the amount of dose applied to an object, storing information including a bag identification, a bag volume, a dose amount, date, and time, and calculating minimum dose time to provide an energy efficient irradiation system, wherein a storage medium will take said bag volume and calculate the minimum dose time. Wherein an ion chamber may intercept and entire or partial amount of x-ray radiation beam to determine actual dose received. Wherein an ion chamber may connect to a plurality of ion chambers in series or parallel and measure dose while irradiation is present. The method wherein storing information in a storage medium allows displaying the amount of dose received to said object on a display apparatus and permitting a user to control a graphical user interface system to increase or decrease the dose. The method wherein an ion chamber can be designed to conform to any shape in a radiation chamber to allow proper passage of radiation.

BRIEF DESCRIPTION OF THE DRAWINGS

FIG. 4 is an illustration of an ion chamber that will be used for real-time dosimetry measurements during blood plasma irradiation.

FIG. 4A is an exemplary illustration of an ion chamber side view, but not limited to the shape shown.

FIG. 4B is an exemplary illustration of an ion chamber top view, but not limited to the shape shown.

FIG. 4C is an exemplary illustration of an ion chamber front view, but not limited to the shape shown.

FIG. 4D is an exemplary illustration of an electrode that is located within an ion chamber, but not limited to the shape shown.

Figure 1:
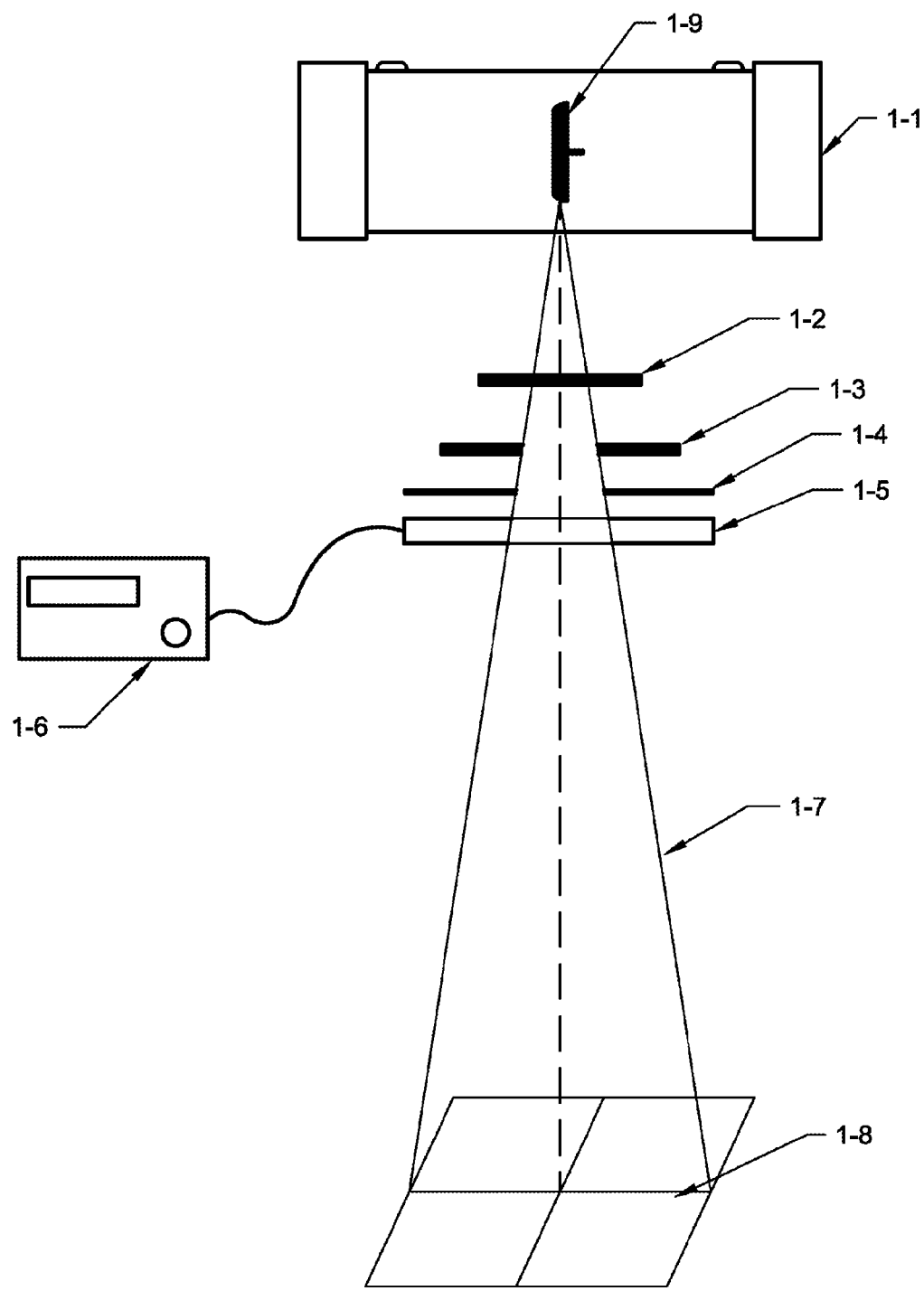
FIG. 1 is a diagram illustrating the factors involved in measuring the Dose-Area-Product, DAP, and the ion chamber location for real-time dosimetry system (RIDS) measurements.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses and/or systems described herein. Accordingly, various changes, modifications, and equivalents of the systems, apparatuses, and/or methods described herein will likely suggest themselves to those of ordinary skill in the art.

Also, descriptions of well-known functions and constructions are omitted to increase clarity and conciseness.

FIG. 1 shows an exemplary Dose-Area-Product, DAP, real-time dosimetry system (RTDS). The x-ray tube 1-9 is located inside the x-ray tube housing 1-1. The x-ray beam 1-7 is emanated from the x-ray tube 1-9, and is passing through a series of x-ray controllers used to restrict the width and length of the x-ray beam 1-7. The x-ray filter 1-2 must intercept the entire x-ray beam 1-7 and is used to remove the lower portion of the x-ray spectrum. Thereafter, the x-ray beam 1-7 will pass through both a vertical leaf collimator 1-3 and a horizontal leaf collimator 1-4. The location of the ion chamber 1-5 is important. The ion chamber 1-5 must be larger than the area of the x-ray beam 1-7. The placement of the ion chamber 1-5, as shown, is post collimation and at a fixed distance from the x-ray source. The ion chamber 1-5 must intercept the entire x-ray beam for an accurate reading. By having the ion chamber 1-5 intercept the entire x-ray beam, the system will be able to determine dose-area-product (DAP). DAP is a quantity that reflects dose and the area of the tissue irradiated. The DAP can be determined by using the electrometer 1-6 that is connected to the ion chamber 1-5. DAP is typically juxtaposed with Exposure-Area-Product but commonly referred to as DAP.

The DAP that reflects dose can be illustrated by Equation 1 or Equation 2:

$$cG_y \times cm^2 \quad \text{[Equation 1]}$$

Here, parameters of Equation 2 may be defined as illustrated by Table 2 below.

TABLE 1

| | |
|---|---|
| $cG_y$ | The dose in centi-Gray, 100 cGy = 1 R. |
| $Cm^2$ | The area, length × width, of the x-ray field |

$$R \times cm^2 \quad \text{[Equation 2]}$$

Here, parameters of Equation 1 may be defined as illustrated by Table 1 below.

TABLE 2

| | |
|---|---|
| R | The dose in Roentegens |
| $Cm^2$ | The area, length × width, of the x-ray field |

DAP is the product of the x-ray dose multiplied by the x-ray field size. This provides a means of recording and tracking the x-ray doses received by patients undergoing various x-ray procedures. The two physical principles apply that make DAP unique: 1—x-ray dose will decreases inversely as the square of the distance from the x-ray source, and 2—the area of the x-ray field will increases as the square of the distance from the source. Thus, when an ion chamber is placed in an x-ray beam at a fixed position from the x-ray source with the ion chamber being larger than the x-ray beam, the product of the dose recorded by the ion chamber multiplied by the area of the x-ray field at this point will be the same at various distances from the x-ray source. This is to illustrated that the DAP calculation estimation, while the ion chamber is used to accurate the measure the dose. This is illustrated in FIG. 2.

Figure 2:
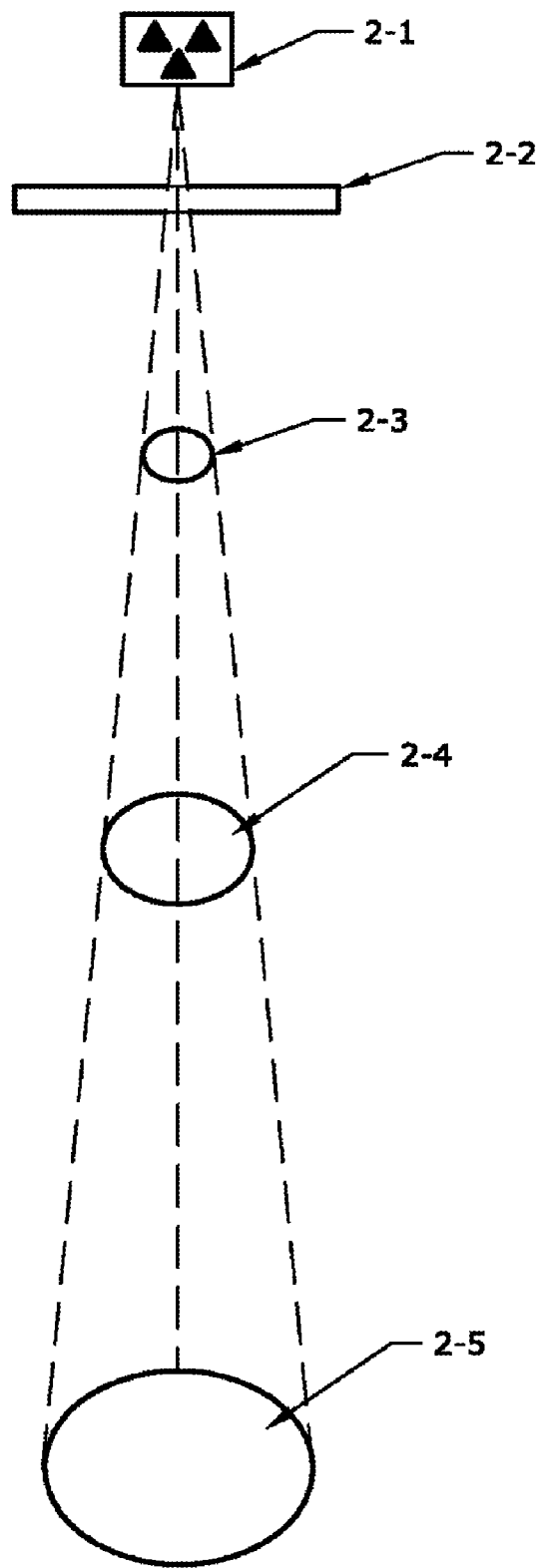
FIG. 2 is a diagram illustrating the value of the dose-area-product (DAP), the product of the x-ray dose and the x-ray field size, will remain the same at various distances from the source

FIG. 2 shows an exemplary illustration that DAP is independent of the distance from the source 2-1. The dose (exposure) from the x-ray source 2-1 decreases inversely as the square of the distance increases from the source while the size of the x-ray field at positions 2-3, 2-4, and 2-5 will increase as the square of the distance from the x-ray source 2-1 is increased. Hence, the product of the dose (exposure) and the field size will remain constant as the distance from the x-ray source is varied. By providing an ion chamber at position 2-2 and using an aperture to fix the size of the x-ray field, the system will be able to measure dose (exposure) at the location of the ion chamber 2-2 and then with a high degree of accuracy and efficiency display the x-ray dose delivered to any of the other locations. For illustrative purposes, position 2-3 may be a distance of 50 cm from the x-ray source, have a beam or field size of 25 cm², and the dose at this position may be 4 Gy. Using Equation 1, multiplying the 25 cm² field size by the 4 Gy dose will yield a dose-area-product of 100 Gy·cm². This dose value will remain unchanged when compared to 2-4. For illustrative purposes only, area 2-4 may be a distance of 100 cm from the source 2-1. Since dose decreases inversely as the square of the distance, the dose at 2-4 will be $(50/100)^2 = (1/2)^2 = 1/4$ of its value at position 2-1, or 4 Gy. The projected field size at position 2-4 will be 4 times as large or 100 cm² since the area of field increases as the square of the distance, $(100/50)^2 = (2)^2 = 4$. Using Equation 1 at position 2-4 we have (1 Gy)×(100 cm²) or 100 Gy·cm². Last, referring to position 2-5, for illustrative purposes, may be a distance of 200 cm. This would give us a dose of 0.25 Gy, $(50/200)^2 = (1/4)^2 = 1/16$ of the 2-1 4 Gy strength. The projected field size would be 400 cm², $(200/50)^2 = 4^2 = 16$, or 16 times larger than 25 cm² field size of position 2-3. Using Equation 1 we have (0.25 Gy)× (400 cm2) or 100 Gy·cm². This clearly demonstrates how the dose-area product remains unchanged at various distances from the x-ray source. By using the equation, dose calculation can be determined, however, using an ion chamber 2-2 measurements reflecting the exact amount of dose delivered to an object at a given distance be made and can reduce energy costs.

Figure 3:
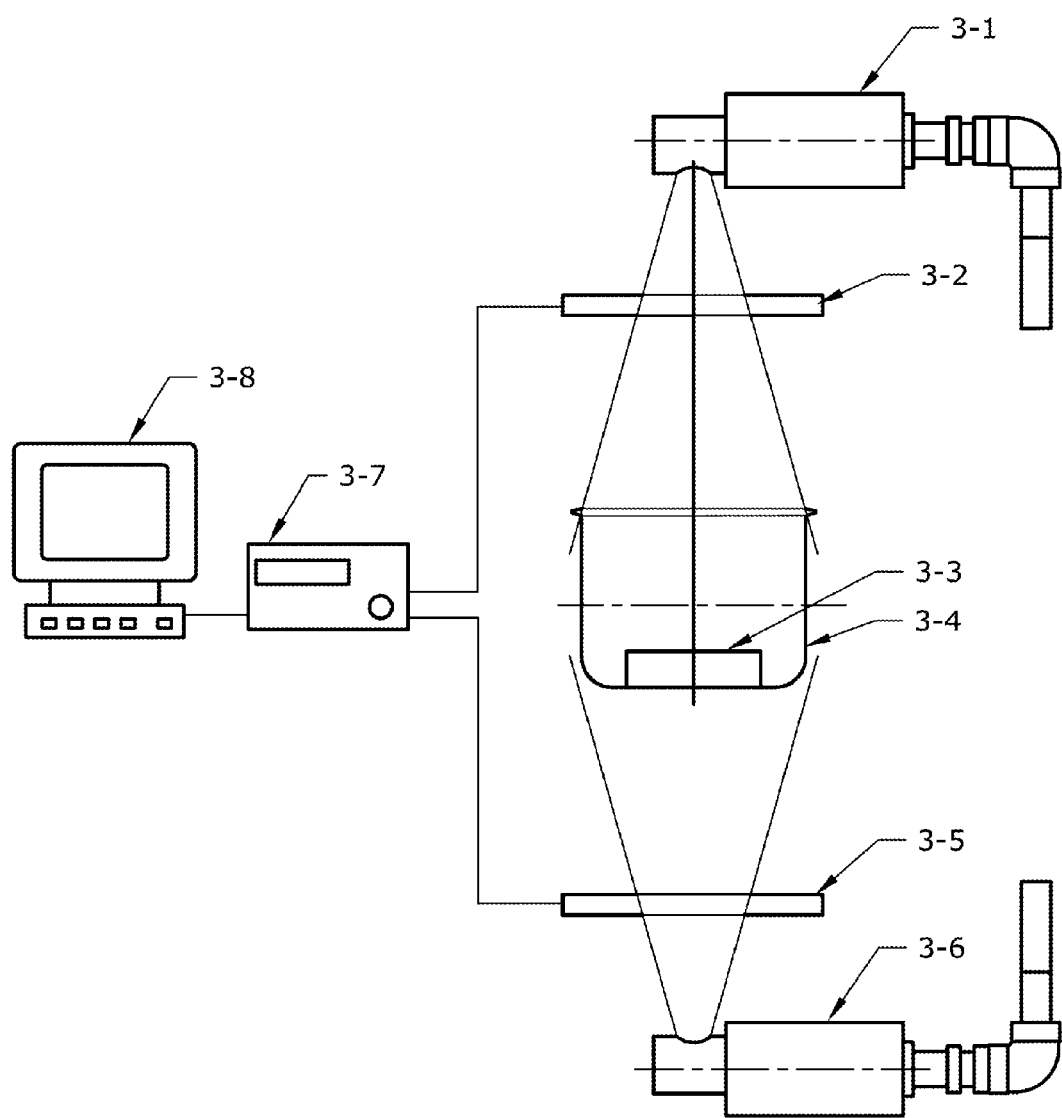
FIG. 3 is a diagram illustrating a real-time dosimetry system (RTDS) that delivers dose during blood plasma irradiation.

FIG. 3 illustrates measurement of two x-ray delivery systems during blood plasma irradiation. Top x-ray tube holder 3-1 and bottom x-ray tube holder 3-2 contain x-ray tubes. The two (2) x-ray tubes are used to simultaneously irradiate an object 3-3. The object 3-3 is held in a container 3-4. The container is constructed such that it allows for uniform exposure of the object 3-3 by both x-ray beams. Top ion chamber 3-2 and bottom ion chamber 3-5 are used to measure the total amount of x-ray dose (exposure) produced during blood plasma irradiation. I segmented ion chambers are use, beam characteristics like flatness and symmetry can be monitored. Both ion chambers, 3-2 and 3-5, will be mounted in a fixed position from the x-ray source such that they completely intercept the entire x-ray beam from each x-ray source. The top ion chamber 3-2 and bottom ion chamber 3-5 will be connected to an electrometer 3-7. The electrometer 3-7 can simultaneously or serially record data from either or both ion chambers depending on the type of configuration. If segmented ion chambers are used, the electrometer can simultaneously or serially record data from the chamber segments from either or both ion chambers depending on the type of configuration. The electrometer 3-7 will then be connected to a computer 3-8 to allow proper dose calculation and real-time control and display of dosage. The computer 3-8 will be able to monitor and determine the amount of radiation delivered to the blood plasma bags. The RTDS monitors and records the radiation dose as it is being delivered to the subject. The advantage to this is that the precise amount of radiation that was delivered to the subject will be known. Thus, variations in delivery system output will be readily apparent and the potential for under or over irradiating all or part of the subject eliminated. If segmented ion chambers are used additional beam parameters can also be monitored. Existing products provide an indication when a minimum radiation dose has been delivered. This is a fixed response point that is chemically controlled and cannot be changed, there are no means to indicate an over irradiation condition, and there is no way to monitor the variations in the radiation output of the delivery system.

FIG. 4 illustrates an ion chamber that is constructed in a circular manner, but can also be constructed in any shape to conform to any system. The ion chamber contains a mounting block 4-3 that holds the guard ring 4-4 and central electrode 4-5. The central electrode 4-5 is shown in FIG. 4D with five segments. The central electrode 4-5 may be partitioned into quadrants or concentric circles if beam parameters such as flatness and symmetry are to be monitored. The central electrode 4-5 has a center dose monitor 4-6, which measure the amount dose. Further, outer dose monitor character beams 4-7 are used to determine the type of beam, the characteristics and distribution. The entrance window 4-2 is made of polyimide, commonly named kapton. The ion chamber is a closed volume filled with air but not sealed. A high voltage, nominally 300 volts DC, is applied between the central electrode, positive, and the entrance window, negative. X-ray photons entering the ion chamber will cause the air molecules to ionize. The negative air ions will be attracted to the positively charged central electrode and the positive air ions will be attracted by the negative charge of the entrance window. This will cause a current to flow in the associated electronic circuit and this current can be measured by an electrometer. Connection to the electrometer is by triaxial connector 4-1. The purpose of the guard ring 4-3 is to precisely define the collection volume of the ion chamber and enhance the ion collection efficiency of the chamber. The material used in the construction of the ion chamber and its internal components allows both the x-ray beams to pass through the ion chamber without causing any noticeable interference and with minimum beam attenuation. This is how the system measures the dose (exposure) and can be used to monitor certain beam parameters.

Figure 5:
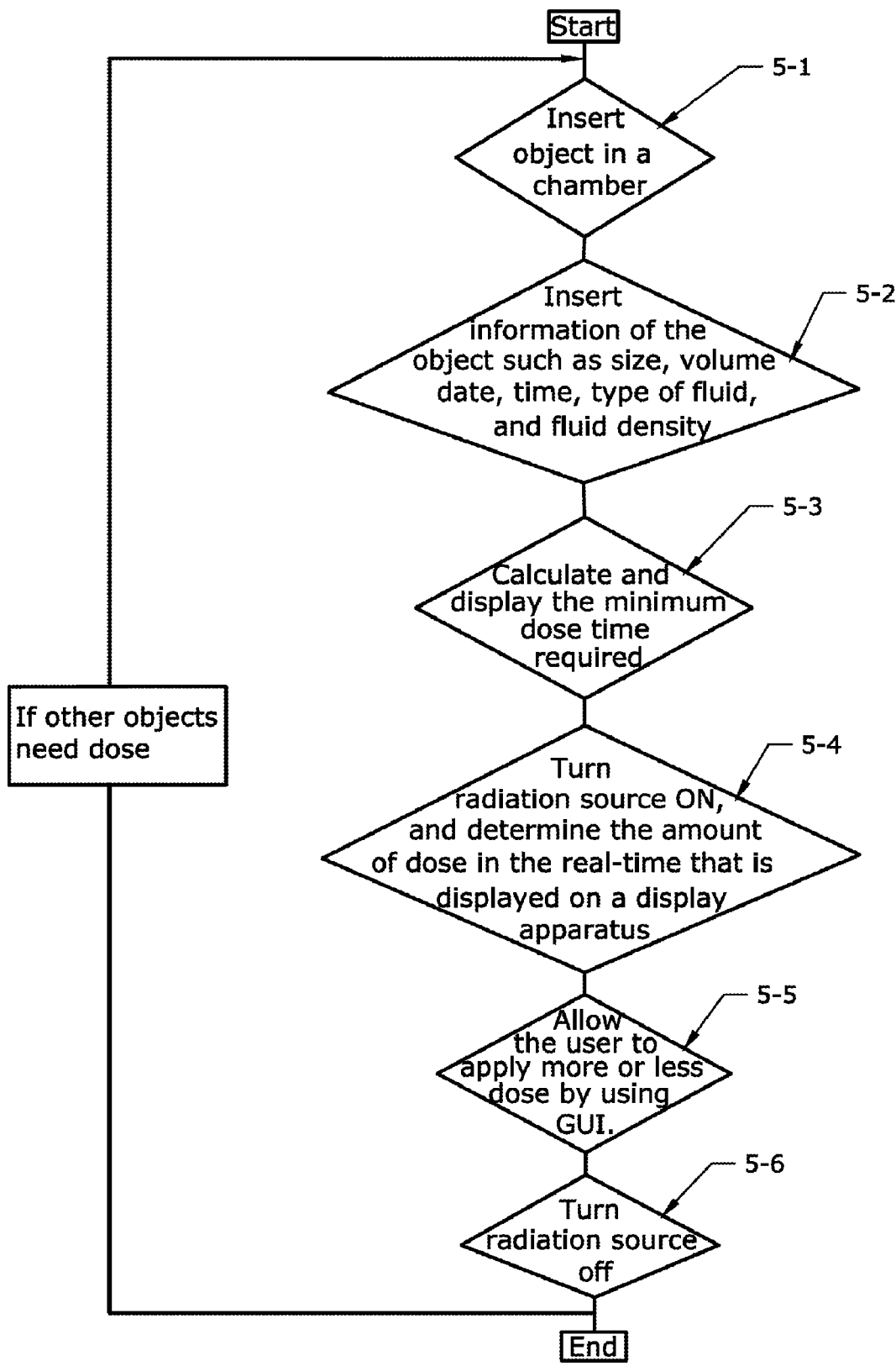
FIG. 5 is an illustration of a process to radiate an object and allowing the user to control the radiation dose while receiving real-time dose measurements.

FIG. 5 illustrates a process of radiating an object and how a real-time dosimetry system can be used to control the radiation source. First, you must insert an object in a chamber 5-1. Then, a user or an individual may record the information of the object such as size, volume, date, time, type of fluid and fluid density into a storage medium. Some systems may use a bar code or unique identifier that will store all the information. The characteristic information is important to allow the storage medium to calculate the minimum dose time required 5-3. When the system determines the minimum dose 5-3, the system may display the information on a display apparatus. Thereafter, the radiation sources are turned on 5-4. As the radiation sources are active, the real-time dosimeter system will display the amount of radiation that is received to the object. The displaying of information will allow the exact amount of dose received and whether the user or the individual would like to apply more or less of the dose amount to the object 5-5. When the system has provided more than the minimum dose requirement, the system will turn off the radiation source 5-6. The termination of the radiation source can be automated or done manually.

As apparent from the above description, loop operating speed may be increased by analyzing commands to be executed, detecting a recurrence node, mapping a recurrence node, a producer node and a predecessor node first, and performing height based order scheduling on the remaining nodes according to ranks of the nodes. Moreover, in view of hardware, specific processing elements are connected through a dedicated path having a fixed delay, and nodes related to recurrence are mapped to such processing elements first, and thus loop acceleration through software pipelining may be maximized.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The invention claimed is:

1. An apparatus to accurately measure blood irradiation comprising:
   an ion chamber used to measure x-rays being radiated from a x-ray source;
   an electrometer connected to said ion chamber used to calculate the amount of dose applied to an object;
   a storage medium used to store information including a blood bag identification, a bag volume, a dose amount, date, and time; and
   said storage medium calculates minimum dose time to provide an energy efficient irradiation system, wherein said storage medium takes said bag volume and calculates the minimum dose time.

2. The apparatus of claim 1, wherein said ion chamber may intercept and entire or partial amount of x-ray radiation beam to determine actual dose received.

3. The apparatus of claim 1, further comprising:
   said ion chamber may connect to a plurality of ion chambers in series or parallel and measure dose while irradiation is present.

4. The apparatus of claim 1, further comprising:
   said storage medium used to display the amount of dose received to said object on a display apparatus and allowing a user to control a graphical user interface system to increase or decrease the dose.

5. The apparatus of claim 1, further comprising:
   said ion chamber can be designed to conform to any shape in a radiation chamber to allow proper passage of radiation.

6. A method to accurately measure blood irradiation, the method comprising:
   measuring the x-ray being radiated from a x-ray source;
   calculating the amount of dose applied to an object;
   storing information including a bag identification, a bag volume, a dose amount, date, and time; and
   calculating minimum dose time to provide an energy efficient irradiation system, wherein a storage medium will take said bag volume and calculate the minimum dose time.

7. The method of claim 6, wherein an ion chamber may intercept and entire or partial amount of x-ray radiation beam to determine actual dose received.

8. The method of claim 6, wherein an ion chamber may connect to a plurality of ion chambers in series or parallel and measure dose while irradiation is present.

9. The method of claim 6, wherein storing information in a storage medium allows displaying the amount of dose received to said object on a display apparatus and permitting a user to control a graphical user interface system to increase or decrease the dose.

10. The method of claim 6, wherein an ion chamber can be designed to conform to any shape in a radiation chamber to allow proper passage of radiation.

* * * * *